(12) United States Patent
Grzeszczuk

(10) Patent No.: US 6,907,281 B2
(45) Date of Patent: Jun. 14, 2005

(54) FAST MAPPING OF VOLUMETRIC DENSITY DATA ONTO A TWO-DIMENSIONAL SCREEN

(75) Inventor: Robert Grzeszczuk, San Francisco, CA (US)

(73) Assignee: GE Medical Systems, Waukesha, WI (US)

( * ) Notice: Subject to any disclaimer, the term of this patent is extended or adjusted under 35 U.S.C. 154(b) by 201 days.

(21) Appl. No.: 09/949,226

(22) Filed: Sep. 7, 2001

(65) Prior Publication Data

US 2002/0082492 A1 Jun. 27, 2002

Related U.S. Application Data

(60) Provisional application No. 60/230,631, filed on Sep. 7, 2000.

(51) Int. Cl.[7] ................................................ A61B 5/05
(52) U.S. Cl. .................. 600/407; 600/417; 600/425; 600/429; 378/41; 378/42; 382/285; 382/294; 382/296
(58) Field of Search ................................ 600/407, 417, 600/425–427, 429; 378/4, 21, 41, 42, 62, 190; 382/285, 296, 300, 302, 294

(56) References Cited

U.S. PATENT DOCUMENTS

| 4,882,679 | A | * | 11/1989 | Tuy et al. ................ 600/425 |
| 5,398,684 | A |   | 3/1995 | Hardy |
| 5,740,224 | A | * | 4/1998 | Muller et al. ............... 378/11 |
| 5,951,475 | A | * | 9/1999 | Gueziec et al. ............ 600/425 |
| 6,016,439 | A |   | 1/2000 | Acker |
| 6,069,932 | A |   | 5/2000 | Peshkin et al. |
| 6,118,845 | A | * | 9/2000 | Simon et al. ................. 378/62 |
| 6,149,592 | A | * | 11/2000 | Yanof et al. ................ 600/427 |
| 6,198,794 | B1 |   | 3/2001 | Peshkin et al. |
| 6,236,875 | B1 | * | 5/2001 | Bucholz et al. ............ 600/407 |
| 6,285,902 | B1 | * | 9/2001 | Kienzle et al. ............. 600/427 |
| 6,470,207 | B1 | * | 10/2002 | Simon et al. ............... 600/426 |
| 6,478,802 | B2 | * | 11/2002 | Kienzle et al. ............ 606/130 |
| 6,546,279 | B1 | * | 4/2003 | Bova et al. ................ 600/429 |

FOREIGN PATENT DOCUMENTS

WO WO 99/00052 1/1999

* cited by examiner

*Primary Examiner*—William C Jung
(74) *Attorney, Agent, or Firm*—McAndrews, Held & Malloy, Ltd.; Peter J. Vogel; Michael A. Dellapenna

(57) ABSTRACT

A method and system for constructing from volumetric CT or MRI scan data of a patient region, a virtual two-dimensional fluoroscopic image of the patient region as seen from a selected point in space are disclosed. In practicing the method, a plurality of rays are constructed between a selected view point and each of a plurality of points in an XY array, where at least some of the rays pass through the patient target region, the points in the XY array correspond to the XY array of pixels in a display screen, and each pixel in the display screen includes multiple N-bit registers for receiving digital-scale values for each of multiple colors. For each pixel element, a sum of all M-bit density values associated with voxels along a ray extending from the selected point to the associated pixel element is calculated. The summing is carried out by distributing the M bits in the voxel density values among the multiple N-bit registers of that pixel, such that such that one or more bit positions of each M-bit value is assigned to a selected register. The image constructed of gray-scale values representing the summed M-bit density values at each pixel in the screen is displayed to the user.

15 Claims, 7 Drawing Sheets

FAST MAPPING OF VOLUMETRIC DENSITY DATA ONTO A TWO-DIMENSIONAL SCREEN

This application claims priority to U.S. Provisional Patent Application Ser. No. 60/230,631 filed Sep. 7, 2000, which is hereby incorporated in its entirety by reference.

FIELD OF THE INVENTION

This invention relates to image-guided surgery, and in particular, to registration and fluoroscopic imaging methods.

BACKGROUND OF THE INVENTION

In a typical image-guided surgical procedure, pre-operative scan data, e.g., CT or MRI scan data, of a patient region is obtained. This is done conventionally by immobilizing a patient during a scan with a CT or MRI imaging machine. The patient is then moved to a surgical setting for treatment of the target region. During the surgical procedure, the scan data is used to reconstruct hidden or subsurface images of the patient target region, to guide or assist the surgeon in the surgical procedure. For example, the scan data may be used to reconstruct a subsurface image of the target region as seen from the position and orientation of a surgical instrument being held by the surgeon.

It is important, of course, for the coordinates of the scan-data images being shown to the surgeon to closely match the coordinates of the actual target region. For this reason, it is important to calibrate the scan data with the actual position of the patient, keeping in mind that the scan data is obtained in one location, and the patient is moved to another location for the surgical procedure. Where the target region is a patient's head region, this coordinate matching may be done by placing fixed-position fiducials on the patient's head during the scanning procedure, and retaining the fiducials at the same head positions for the surgical operation. Coordinate matching can then be done by aligning the positions of the fiducials in both reference frames. This approach relies on the fact that the fiducials placed on rigid, non-deformable structure (e.g., skull) are retained in substantially the same position (patient coordinates) for both the scanning and surgical procedures.

For other surgical regions, e.g., the spine, it is virtually impossible to retain fiducials at fixed patient coordinates between the scanning and surgical operations. In this case, it is necessary to recalibrate the positions of the fiducials in the patient coordinate system every time the patient moves or is moved. Ideally, the surgeon would want to forego the use of fiducials altogether, since their placement involves additional inconvenience to the patient and surgeon.

It would therefore be useful to provide an improved system for registering pre-op scan data in a patient coordinate system during a surgical operation, to be able to use the scan data to accurately construct subsurface image data corresponding to the actual patient coordinate system.

Also during a surgical operation, a surgeon will often wish to check the exact placement of surgical cut, or placement of a tool or implant at the patient site. This can be done conventionally, by taking a fluoroscopic image of the patient region, and displaying the 2-D image to the surgeon. Unfortunately, the surgeon will be limited in the number or times and duration of fluoroscopic imaging, due to the need to limit the amount of x-ray exposure to both the patient and medical personnel.

It would therefore be desirable to provide a method and system of virtual fluoroscopy that allows a surgeon to view a patient region "fluoroscopically" from a number of different angles, and over extended periods of view, without actually exposing the patient and others in the surgical theatre to exposure to x-rays.

In particular, it is would be useful to construct virtual fluoroscopic images in real time, e.g., without significant computation time.

SUMMARY OF THE INVENTION

The method includes, in one aspect, a method for constructing from volumetric CT or MRI scan data of a patient region, a virtual two-dimensional fluoroscopic or shadowgraph image of the patient region, as seen from a selected point in space. The method includes the steps of selecting a point in space representing a virtual fluoroscopic irradiation source, and defining a plurality of rays extending between the source point and each of a plurality of points in a two-dimensional XY array of points, where (i) the array points correspond to pixels in an XY pixel array in a display screen called a framebuffer, (ii) each pixel in the display screen has multiple N-bit registers for receiving digitized values for each of multiple colors, (iii) the scan data consists of voxels having defined coordinates and associated M-bit tissue-density values, and (iv) at least some of the rays pass through a plurality of such voxels in the patient target region.

For each ray, the bit positions of the M-bit voxel density values along that ray are distributed among the multiple N-bit registers of the associated pixel, such that one or more bit positions of each M-bit value is assigned to a selected register of that pixel. The M-bit density values of the voxels are summed along that ray by (i) individually summing the one or more bit-position values in each associated pixel register, and (ii) determining the sum of the M-bit values along the associated ray from the values in the individual registers. The image constructed of gray-scale values representing the summed M-bit density values at each pixel are displayed on the display screen.

Where the pixel elements in the graphics screen each contain four 8-bit registers, corresponding normally to blue, green, red and alpha registers, the density values in each voxel are 8-bit numbers, and the bit positions of the 8 bit voxel-density values are distributed, for example, (a) two digits each to each of the registers, or 3 digits, 3 digits, 1 digit and 1 digit to the four registers.

In a related aspect, the invention includes a system for constructing from volumetric CT or MRI scan data of a patient region, a virtual two-dimensional "fluoroscopic" or shadowgraph image of the patient region as seen from a selected point in space. The system includes a scan-data file for storing, in digital form, volumetric scan data of a surgical site of a patient, where the scan data consists of voxels having defined coordinates and associated M-bit tissue-density values, and a display screen containing a two-dimensional XY array of pixel elements, each element containing multiple N-bit registers for receiving digital-scale values for each of multiple colors.

A computational device in the system is operatively connected to the data file and display screen for (i) defining a plurality of rays extending between a selected source point and each of a plurality of points in a two-dimensional XY array, where (ia) the array points correspond to the array pixels in the display screen, and (ib) at least some of the rays pass through a plurality of scan-date voxels in the patient target region, (ii) for each ray, distributing the bit positions of the M-bit voxel density values among the multiple N-bit registers of the associated pixel, such that one or more bit positions of each M-bit value is assigned to a selected register of the associated pixel, (iii) for each ray, summing the M-bit values of the voxels along that ray by (iiia) individually summing the one or more bit-position values in each associated pixel register, and (iiib) determining the sum of the M-bit values along the associated ray from the values in the individual registers, and (iiic) plurality of passes over the previous step to further reduce a chance of register overflow and (iv) applying the summed tissue-density values along each ray to the associated pixel in the display screen.

These and other objects and features of the invention will become more fully apparent when the following detailed of the invention is read in conjunction with the accompanying drawings.

DETAILED DESCRIPTION OF THE INVENTION

Figure 1:
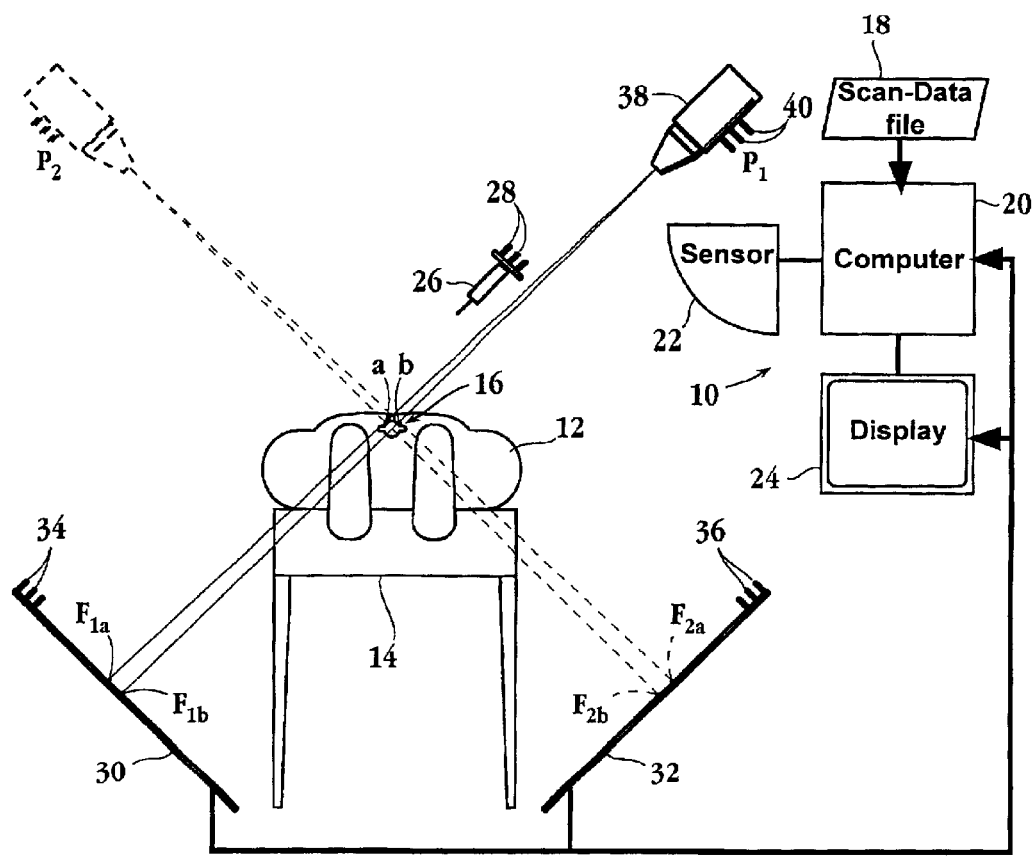
FIG. 1 illustrates an arrangement of components of a surgical imaging system and a patient in a surgical setting containing the system.

The present invention is designed to enhance several aspects of image-guided surgery. In each case, the invention depends on or uses pre-operative volumetric scan data of a patient target region. Typically, the scan data acquired are computerized tomography (CT), magnetic resonance imaging (MRI), or ultrasound scan data, obtained according to well-known methods. The scan data are conventionally stored in digitized form in a scan-data file, for later use in the invention. For purposes of the present invention, the scan data have three important characteristics.

First, the target region (volume) that is scanned is divided into a three-dimensional voxel space, where each voxel (small volume element) typically represents an x-y element in the "plane" of scans taken along the z direction. (Voxels defined by other types of coordinate systems, e.g., polar coordinates, may also be employed). Second, each voxel is associated with an M-bit density value that characterizes the scan density observed for that volume element in space. Third, the voxel coordinates are placed in a patient coordinate system keyed to one or more of the following: (i) patient structural features, such as bone features or external surface features, (ii) fiducials, typically small metal markers, implanted at selected positions within the patient target region, (iii) fiducials placed at fixed positions on the surface of a patient, or (iv) sensor elements placed at fixed positions in or on the patient.

During a surgical procedure—that is, after the patient has been moved from a scanning station to a surgical station— the scan data must be placed in the new patient coordinate system. This is done, in general, by determining the coordinates of patient physical structure, e.g., bone features or fiducials, and transforming the coordinates of the scan-data voxels to the new coordinate system.

Various approaches to placing pre-op scan data in registration with the patient surgical position have been proposed heretofore. In one, fiducials whose position in space can be determined by a fixed-position sensing unit are placed on the patient. The fiducial positions in the surgical setting can then be determined directly by the sensing unit, and used as reference points for the scan data, which includes images of the fiducials at known voxel positions. The limitation with this method, at least in spinal surgery, is that the fiducials must be placed on the patient surface, and typically do not provide accurate coordinates for subsurface structure, e.g., vertebrae.

In a second approach, a fluoroscopic image of the patient target region is produced on a display screen, and this image is then position-matched with a digitally reconstructed radiograph (DRR) produced by reconstructing scan data. By manipulating the coordinates of the scan data until the DRR and actual fluoroscopic image match, scan data coordinates corresponding to actual patient coordinates are obtained. This method is described, for example, in U.S. Pat. Nos. 4,791,934 and 5,901,199. One aspect of the present invention, described in Section II below, is a fast-mapping algorithm that significantly reduces the time needed to generate virtual radiographic images, and thus significantly improves this image-matching method.

A third approach, which forms another aspect of the present invention, is described in Section I below.

I. Registering Pre-Op Scanning Data with Patient Position

FIG. 1 illustrates components of a system 10 of the invention, shown in operative relationship to a patient 12 placed face-down on a surgical table 14. For purposes of illustrating the describing the invention, the patient region of interest—the surgical target region—is the patient's spine, indicated at 16. Although the invention is applicable to any patient target region, the invention is particularly applicable to spinal region, both because the vertebrae of the spine offer a good fluoroscopic target (bone), and because the position of the spine is difficult to track by external markers when the patient moves or is moved. The same applies to any piecewise rigid structure (e.g., any part of skeletal anatomy).

System 10 includes a data-scan file 18 which stores pre-op scan data, typically obtained at a scanning station (not shown) which is different from the surgical station shown. As indicated above, the scan-data consists of voxel coordinates, corresponding scan-data, e.g., density values, for each voxel, and coordinates for registration features, e.g., selected bone features or fiducials. The scan data file is operatively connected to a computational device 20, e.g., computer or processor, which carries out the data processing operations of the system, to be described. Also connected to the computer are a fixed-position sensing unit 22 and a display device 24. The display device is preferably includes a conventional computer color-monitor screen composed of a framebuffer with an XY array of pixels, where each pixel has four N-bit registers, e.g., 8-bit registers, corresponding to red, green, blue and alpha registers.

Sensing unit 22 is part of a position tracking system, which is preferably an optical tracking system (hereafter "OTS") having sensing unit 22 mounted overhead in view of the operating table scene, and various movable objects, each equipped with at least two light emitting diodes (LED's) mounted on the object. In the embodiment shown, the movable objects include first and second detecting plates 30, 32 designed to be placed at selected positions adjacent the patient, as shown, and an x-ray source 38 also designed to be placed at selected position with respect to the patient. Another movable object that may be included in the system, but which is not necessarily used for registration, is a surgical instrument 26 designed to be used by the physician during a surgical procedure.

As shown, X-ray source 38 is equipped with LED's 40; screen 30, with LEDs 34; screen 32, with LEDs 36, and instrument 26, with LEDs 28. The LED's attached to the movable objects are preferably designed to emit streams of pulsed infrared signals which are sensed by a plurality of infrared detectors (not shown) contained in the sensing unit. The sensing unit and movable objects are connected to the computer, which controls the timing and synchronization of the pulse emissions by the LED's and the recording and processing of the infrared signals received by the detectors. The OTS further includes software for processing these signals to generate data indicating the location and orientation of the movable objects in the frame of reference of surgical station. The OTS may generate the position data on a real-time basis, so that as the surgical instrument is moved, for example, its position and orientation are continually tracked and recorded by the sensing unit, and when the display screens or x-ray source are moved, their positions in the coordinate system of the surgical station are known.

The OTS is preferably of the type known as the "Flash-Point 3-D Optical Localizer", which is commercially available from Image Guided Technologies of Boulder, Colo., similar to the systems described in U.S. Pat. Nos. 5,617,857 and 5,622,170. However the invention is not limited to this particular OTS, and other position tracking systems, such as sonic position detecting systems, may also be utilized.

X-ray source 38 may be, for example, any of a number of commercially available fluoroscopic sources such as an OES 9600 obtained from General Electric Medical Systems (Milwaukee, Wis.). The source is typically mounted on a suitable frame (not shown) for positioning at a selected "view" position with respect to the patient. The detecting plates may be, for example, conventional rectangular arrays of CCD devices or other electronic components that convert radiation intensity into corresponding electronic signals. The CCD elements in the plates are operatively connected to corresponding pixel elements in the display screen, for displaying the fluoroscopic or shadowgraph image of the patient region projected onto the detecting plate. For example, if the CCD devices output an 8-bit digital signal, this output can be supplied to one of the four display screen registers to display the CCD array output on the display screen. Also as indicated in the figure, the CCD elements making up the arrays in each detecting screen are connected to computer 20, for supplying the computer with digitized fluoroscopic data recorded at the array positions on the plate.

Ultimately, and as described further below, the system will be used to display patient target-region images reconstructed from the scan data and as seen, for example, from the position and orientation of instrument 26, for guiding the physician during a surgical operation.

Figure 2:
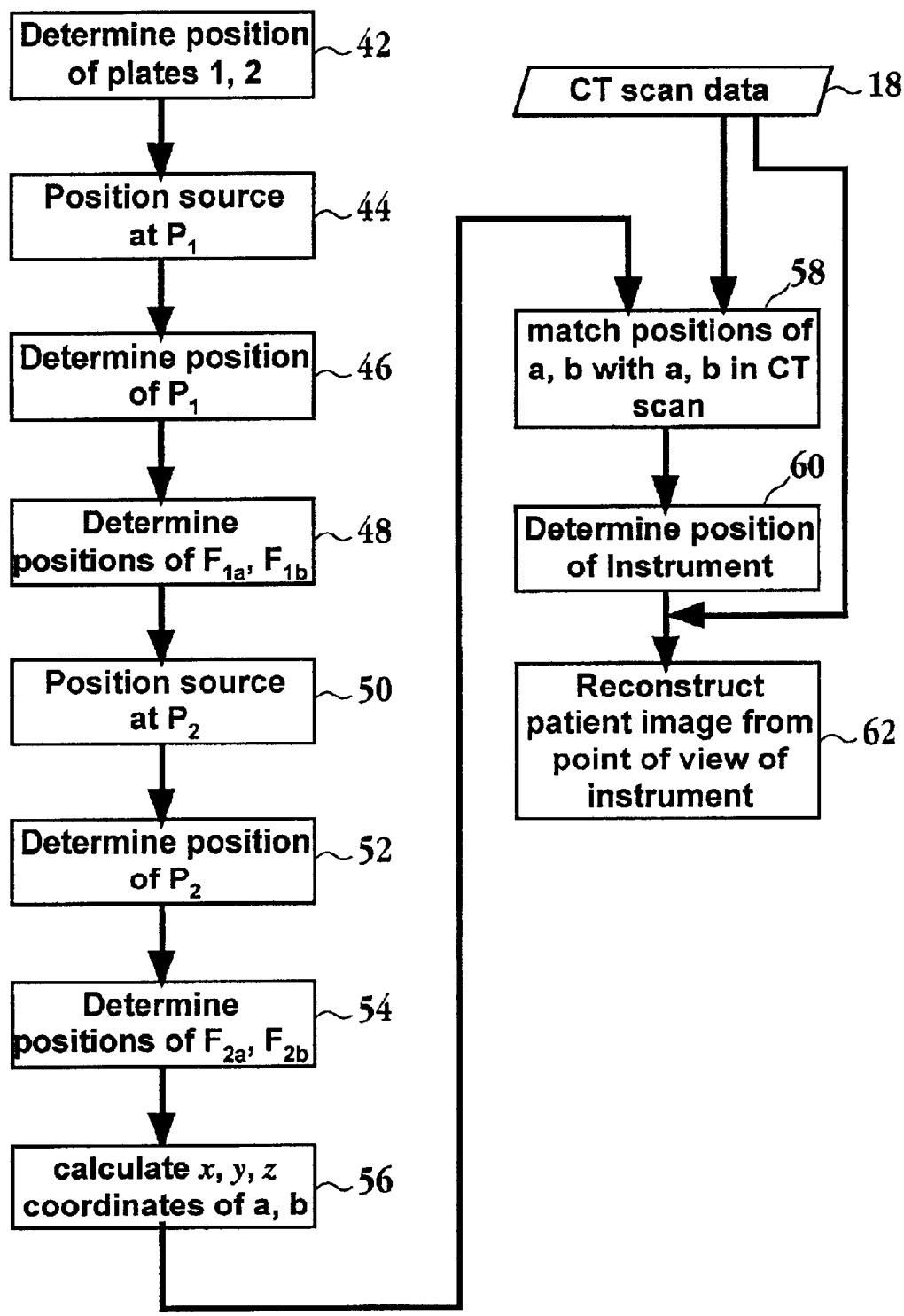
FIG. 2 is a flow diagram of steps executed by a computational device in the system, for registering pre-op scan data with actual patient position, and for using the scan data to construct target images from a selected position and orientation.

The registration method of the invention is illustrated in FIG. 1, and the steps in practicing the method, including those steps executed by computer 20, are given in the flow diagram in FIG. 2. Initially, source 38 and plate 30 are positioned at selected positions to image the patient target region, e.g., spinal region, from a first selected position, as illustrated in FIG. 1. With the source and plate so positioned (the source position is indicated at $P_1$) the OTS is activated to record the positions of both source and plate in the frame of reference of the sensing unit, that is, with respect to a fixed point of reference within the surgical station. The X-ray source is then activated to produce a fluoroscopic image or shadowgraph of the patient region, as detected at the detector plate. The array signal intensity data is supplied to display 24, for displaying the fluoroscopic image to the user, and also input into a dedicated image file in computer 20.

At this point, the system (with or without the users assistance) identifies three or more patient-region features that are also recognizable in the pre-op scan data. The features may be, for example, radio-opaque fiducials, which can be identified by their high-density values, or bone features that can be identified by their distinctive shape or position. The user may specify these features by "clicking" on these features in the image displayed in device 24, or the features may be "recognized" by the system automatically according to distinctive density values, e.g., by sharp density-edge effects. Once the features have been identified, the system records the XY positions of the features on the display screen, corresponding to the XY positions on the detector plate.

The source and detector plate are now shifted to second selected positions for viewing the target region from a second angle. In the embodiment shown, source 38 is moved from $P_1$ to $P_2$, and the detector plate (which may be the same plate 30 or a second plate 32) is moved to the position shown for plate 32. A second fluoroscopic image of the target region is then taken, with the image being displayed to the user at device 24 and stored in the processor as above. Again the system or user identifies the same target features identified earlier, and the positions of these features on the detector plate are stored.

The program flow in FIG. 2 shows how the system determines the actual spatial coordinates of the patient features, e.g., features a, b in FIG. 1. Initially the spatial coordinates of the detector plate(s) at both views are determined by the OTS and stored in the computer, as at 42. Source 38 is then positioned at selected position $P_1$, as at 44, and its coordinates determined by the OTS, as at 46. The source is activated to produce a fluoroscopic image or shadowgraph on detector plate 30. The positions of features a, b in the shadowgraph are indicated at $F_{1a}$ and $F_{1b}$ in FIG. 1, corresponding to positions $x_{1a}, y_{1a}$ and $x_{1b}, y_{1b}$ on the detector plate array, and to pixels $x'_{1a}, y'_{1a}$ and $x'_{1b}, y'_{1b}$ on the display screen. From the known x,y positions of features a, b on plate 30, and from the known position of the plate, the computer determines the coordinates of $F_{1a}$ and $F_{1b}$ ($x_{1a}, y_{1a}$ and $x_{1b}, y_{1b}$) by standard geometric calculations, as at 48, and these coordinates are stored in the computer for later use.

Similarly, after moving the source to selected position $P_2$, as at 50, and determining the new source position, as at 52, and with detector plate 32 at a second selected plate position, the user takes a second fluoroscopic image of the patient region from this second selected view. The second image contains the features of interest, e.g., a, b, as indicated at $F_{2a}$ and $F_{2b}$, in FIG. 1. As above, from the known positions of these features on the detector plate, and from the OTS determined position of the plate, the coordinates of $F_{2a}$ and $F_{2b}$ are determined, as at 54.

The program now has the x,y,z spatial coordinates for the two source positions $P_1$ and $P_2$, and for the plate coordinates of the patient features on both plates (or one plate at two selected position), e.g., $F_{1a}$ and $F_{1b}$ and $F_{2a}$ and $F_{2b}$. These coordinates allow the program to calculate, by standard "intersection" equations, the x,y,z coordinates of selected patient features, e.g., a, b, as at 56.

The system next determines the scan-data coordinates for the same patient features in the scan data file 18. This may be done, in one embodiment, by reconstructing a virtual image from the scan data, and having the user "click on" the feature(s), e.g., implanted fiducials or distinctive bone features, used as landmarks in the fluoroscopic images, e.g., features a, b. Alternatively, the program may automatically identify the landmark features by distinctive density values or density patterns, as above.

Once the selected features or landmarks in the scan data are identified, the program will construct a transform that transforms the internal coordinates of these features into the spatial coordinates of the features determined from the fluoroscopic images, as at 58. This transform, when applied to all of the scan-data coordinates, effectively places the scan-data in the actual frame of reference of the patient. That is, the scan data is placed in registration with actual patient position.

After executing this transformation, the system can use the scan data to construct selected subsurface views, e.g., perspective views) of the patient target region, corresponding to the actual patient position. These images may be presented to the physician at display device 24. In one preferred embodiment, the OTS in the system is used to track the real-time position of a surgical tool or instrument, e.g., instrument 26, and the reconstructed images are be displayed from the position and orientation of the instrument, allowing the user to view hidden tissue and the instrument is moved toward or within the patient target site. Methods and algorithms for producing such images, particularly as seen from the point of view of a movable instrument, are described, for example, in PCT application WO 9900052 A1 for Image generation of three dimensional object, which is incorporated herein by reference.

II. Fast 3-D to 2-D Mapping Method and System

In another aspect, the invention provides a rapid method for mapping 3-D scan data onto a 2-D display format, particularly for use in generating digitally reconstructed radiographs (DDRs) or virtual shadowgraphs from CT, MRI or ultrasound volumetric scan data. Such radiographs are also referred to herein as virtual fluoroscopic images or virtual shadowgraphs, meaning a displayed image that resembles a fluoroscopic image taken from a selected view, but which is constructed from pre-op scan data rather than actual x-irradiation of the patient site.

The system for carrying out the invention generally includes the components shown in FIG. 1, in particular, a scan data file 18, computational device 20, and display device 24. As described above, the scan file consists of voxel coordinates, corresponding scan-data, e.g., density values, for each voxel, and coordinates for registration features, e.g., selected bone features or fiducials. The scan data file is operatively connected to the computational device, e.g., computer or processor, which carries out the data processing operations of the system to be described.

The display device is preferably a conventional computer color monitor having a display screen composed of an XY array of pixels, e.g., a 1280×1024 pixel array. The frame-buffer provides, for each pixel, a plurality of N-bit registers, typically four 8-bit registers corresponding to blue, red, green, and alpha single-valued pixel input values. Each pixel register functions to accept an N-bit color value, for outputting to the corresponding pixel, an electronic signal indicating the corresponding brightness of that color in that pixel. According to an important requirement of the invention, each register is hardwired with an "add" function that allows the register to add successive values (with N or fewer bits) supplied to the register. Virtually all commercially available color monitors have these features and are therefore suitable for use in the invention.

In the present system, the computer is connected to the monitor to provide input to all of the pixels, and to each of the registers in each pixel element, simultaneously, to allow parallel input to each pixel during the operation of the system. The operation of the computer, and the computer software or hardwired program required in the system in the system will be appreciated below from the description of the method carried out by the system, with reference to FIGS. 3–7.

It is assumed in the following discussion that it is desired to construct a virtual fluoroscopic image of a spinal target region 16 in patient 12, and that the view of the target tissue is that which would be produced by projecting x-rays from a selected source point $P_1$ onto a detector screen placed at the position occupied in the figure by a virtual detector plate, indicated at 64. The virtual plate is considered as an array of points, such as points 64, 66, corresponding to the CCD elements in an actual detector plate array, and each point is designated by a unique x,y coordinate in the array. That is, all points in the array can be represented by coordinates $x_i, y_k$, i=1 to m, and j=1 in an m×n array. Further, the points correspond, through a one-to-one mapping, to the pixels in the XY pixel array of the display device.

Figure 7:
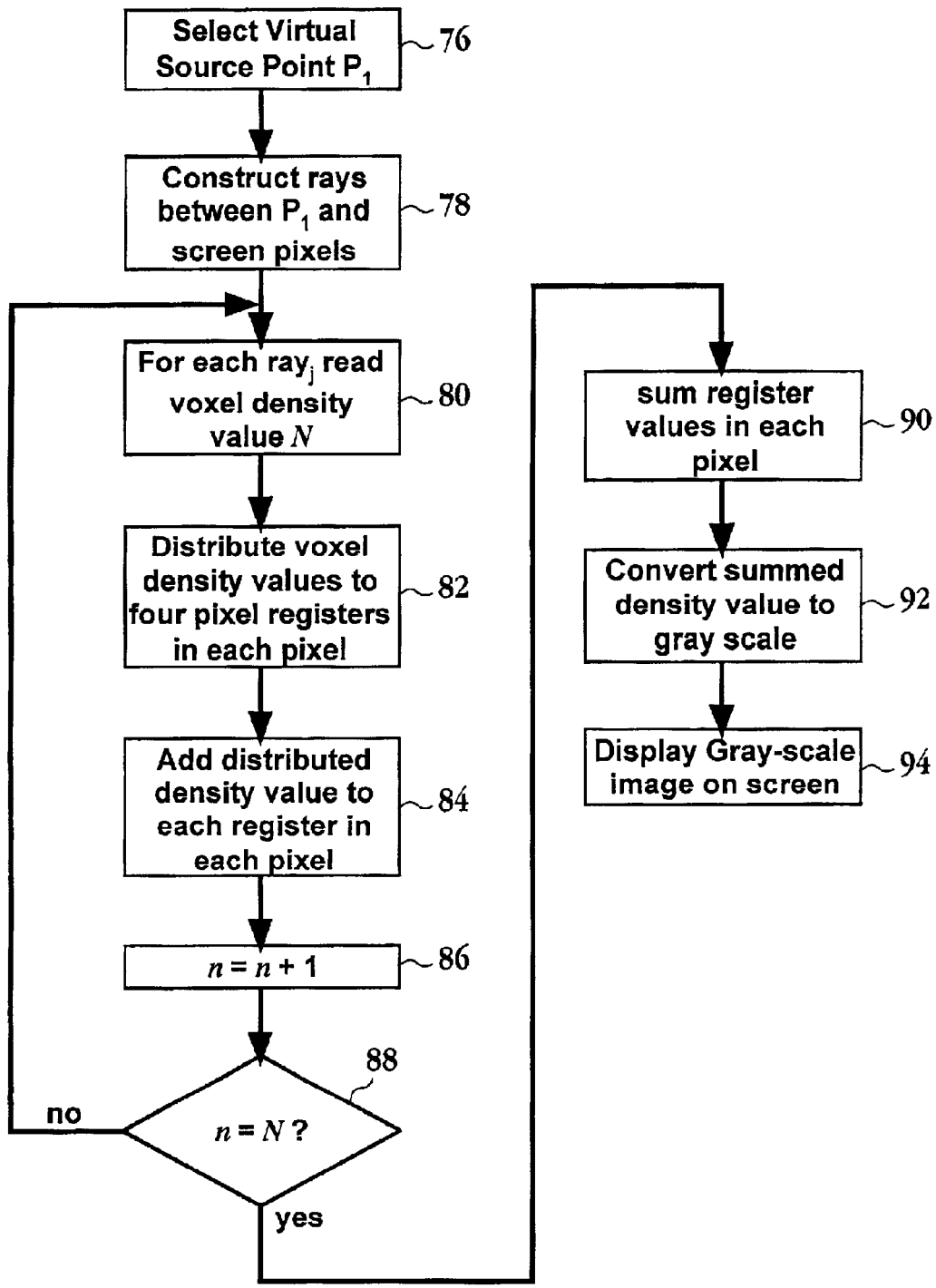
FIG. 7 is a flow diagram of the fast mapping method in accordance with the invention.

In practicing the method, the user selects a desired source point $P_1$ from which the patient target tissue will be viewed, as at 76 in FIG. 7. This may be done, for example, by providing a movable frame-mounted pointer that can be moved to a selected point with respect to the patient, allowing the field of view angle to be selected according to the distance between and pointer and the patient, and the view orientation to be selected according to the orientation of the pointer. The position and orientation of the pointer may be tracked by the above OTS (or comparable tracking device) to indicate to the computer the actual coordinates of the virtual source point $P_1$. In particular, the pointer can be rigidly fixed to the exterior of the real fluoroscopic camera to allow for natural simulation of its use. Similarly, it can be hand-held to permit computing views that would not be possible to physically realize with a real fluoroscope (e.g., axial views).

Figure 3:
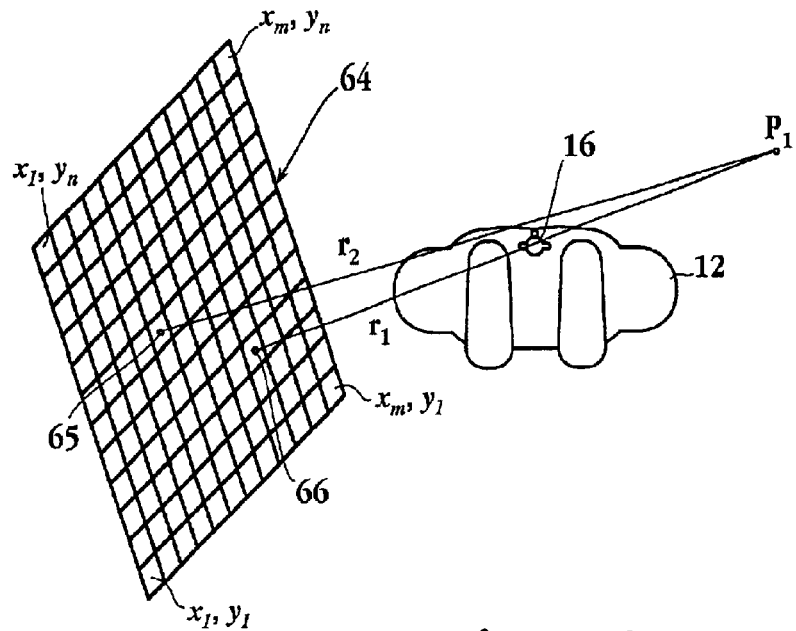
FIG. 3 shows the projection of rays through a target region onto a virtual array from a virtual source point, in the method of the invention for constructing virtual fluoroscopic images.
Figure 4:
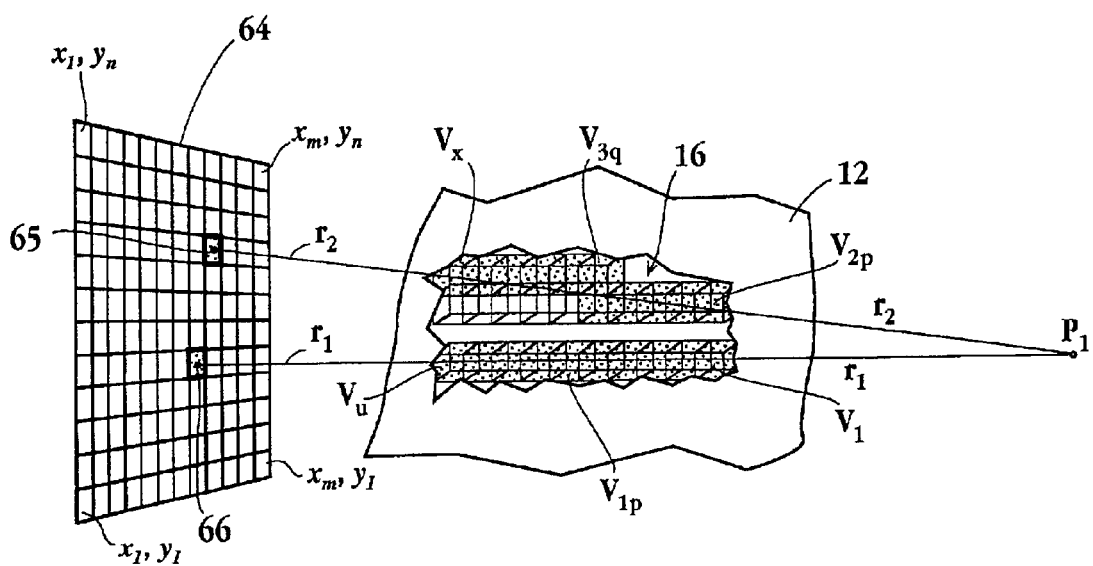
FIG. 4 illustrates the use of voxel elements in calculating pixel density values, in constructing a virtual fluoroscopic image in accordance with the invention.

With virtual source point P1 selected, the computer constructs a set of rays as at 78 in FIG. 7. FIGS. 3 and 4 show exemplary rays $r_1$ and $r_2$ in such a construction. The computer selects the coordinates of the virtual detector points so that at least a portion of the rays pass through the target region of interest, as shown in FIG. 3. Preferably the cross-section of the rays encompasses the entire target region, and a central ray is normal to the plane of virtual plate.

In constructing the virtual fluoroscopic image, the program operates to sum the scan-data density values along each ray in the set of rays, and place this sum (after scaling)

in one of the registers, e.g., the gray-scale register of the corresponding pixel in the display device, to display the virtual fluoroscopic image to the user. In order to perform this summing operation, the program must define a frame of reference for the scan data, so that each voxel in the scan data can be assigned to one or more rays projecting through the patient target region. If the scan data has been placed in registry with the patient position, as described above, the coordinates of the scan data voxels can be assigned actual patient coordinates in the surgical setting. If no such registration is performed, or if the patient moves after the registration operation, the voxel coordinates may correspond approximately, but not precisely, to actual patient coordinates.

FIG. 4 illustrates the assignment of voxels to rays r1 and r2, as representative of all of the rays considered in the method. The computer knows the actual x,y,z coordinates of P1, and has assigned x,y coordinates to each of the points in the virtual detector array. (The z axis is considered here as the axis normal to the plane of the virtual detector array). Therefore, the x,y position of each ray at each scan slice (along the z axis) is known and assigned a voxel corresponding to the x,y,z coordinates of the ray at that slice position (z coordinate). As noted above, the voxel coordinates may be actual patient coordinates, or may be coordinates assigned when the scan data was obtained. For some rays, such as ray $r_1$, the ray may extend through a single column of voxels in the patient target region, such as the voxels identified in FIG. 4 as V1$p$, where p=1 to w; for others, such as ray $r_2$, the ray may extend through two or more voxel columns, such as the columns identified by voxels $V_{2p}$ (p=1 to y) and the adjacent voxel column made up of voxels $V_{3q}$, q=1 to x). Alternatively, the voxels may be assigned polar coordinates, such that each ray passes through a single column of voxels.

Each of the voxels is associated with a tissue-density value representing the tissue density seen by the scanning device at that voxel position. The density value is scaled, if necessary, to a selected M-bit number, preferably an 8-bit number to represent, for example, 255 different density values. The program then operates to sum the density values along each ray, to produce a summed value representing the total tissue density that an x-ray would encounter on traversing the associated column(s) of voxels in the patient target region.

Figure 5:
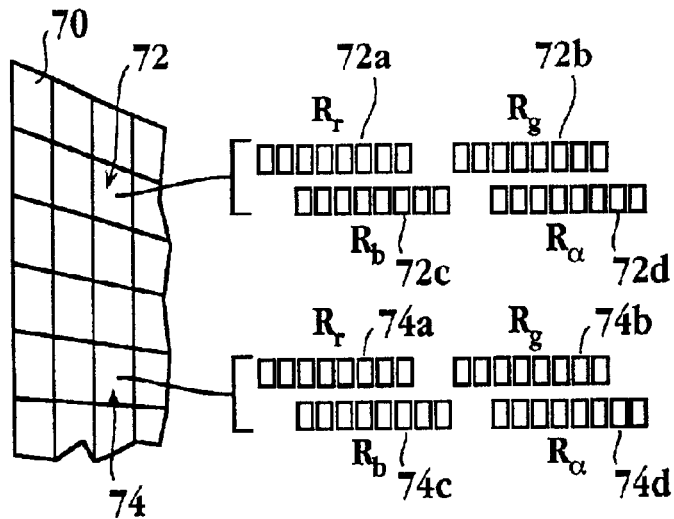
FIG. 5 shows four registers associated with each pixel element in a display screen employed in the present invention.
Figure 6:
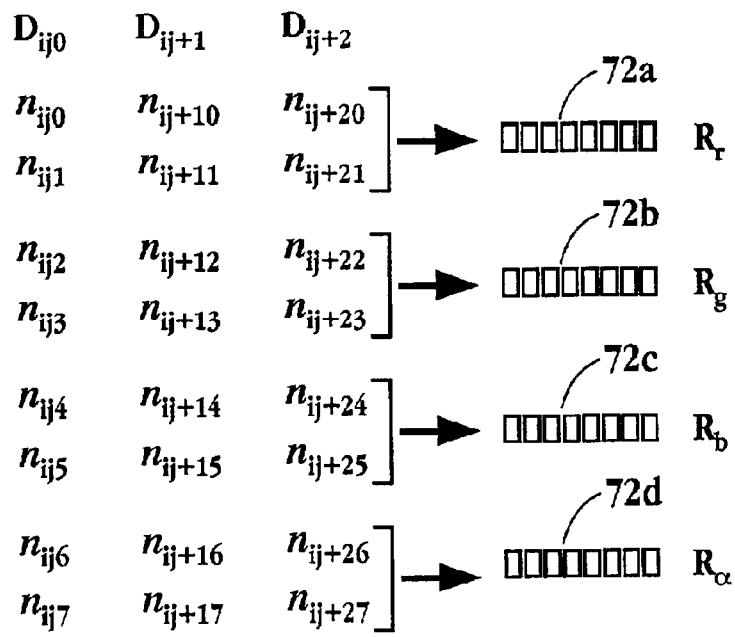
FIG. 6 shows one assignment of density-value digits to display-screen registers in the method of the invention.

The summing operation along the rays is carried out in parallel for all rays, whereby the total summing operation time is no greater than that required for a single ray. According to an important feature of the invention, the summing operation is further accelerated by taking advantage of the ability of the pixel registers to sum values applied to the registers. How this feature is exploited in the present invention is illustrated in FIGS. 5 and 6. FIG. 5 shows a portion of a display screen 70 having an XY array of pixels, such as pixels 72, 74 corresponding to the XY array of points in the virtual detector array in FIGS. 3 and 4. Each pixel, such as pixel 72, receives input from four N-bit registers, such as registers 72$a$, 72$b$, 72$c$, and 72$d$ associated with pixel 72 and registers 74$a$, 74$b$, 74$c$, and 74$d$ associated with pixel 74. In the normal color-display mode of the display device, the four registers operate to signal impart a particular color to each pixel, depending on the relative values supplied to the pixel by the four registers.

Typically, the pixel registers are 8-bit registers, and therefore capable of holding up to 255 different digitized values. In the discussion below, 8-bit registers will be assumed, although it will be recognized that the summing operation could be applied to larger registers, e.g., 16-bit registers.

For each ray, the summing operation is carried out by first considering the 8-digit density value as four separate 1-, 2-, or 3-bit numbers. The reason for splitting the input values this way is to reduce the possibility that any of the individual registers will overflow. The four smaller values, representing particular bit positions in the 8-bit number, are then assigned to the four color registers. For example, in the assignments illustrated in FIG. 6, the 8-bit density-value number is broken down to four two-bit numbers, such that the 8-bit number $n_7n_6n_5n_4n_3n_2n_1n_0$ becomes $n_7n_6$, $n_5n_4$, $n_3n_2$, and $n_1n_0$, with each of the 2-bit numbers being assigned to one of the four registers. Another preferred assignment considers the 8-bit number in two groups or three digits and two groups of one digit, such that the 8-bit number $n_7n_6n_5n_4n_3n_2n_1n_0$ become $n_7n_6n_5$, $n_4n_3n_2$, $n_1$, and $n_0$, again with the four smaller numbers being assigned to the four pixel registers. An advantage of the later bit distribution is that lowest-bit numbers, e.g., $n_1$, and $n_0$, are expected to include higher noise values, and thus may overflow the associated registers faster during a summing operation, than do the higher-bit numbers. By limiting the lower-bit numbers to one bit positions, the tendency to overflow the associated registers is minimized.

In a summing operation, illustrated in FIG. 6, the first voxel 8-bit number in each ray (n=1) is read, as at 80 in FIG. 7, and is placed in the four registers of the corresponding display pixel, in accordance with the above bit assignments, such that each register receives a 1-, 2-, or 3-bit number, as at 82 and 84 in FIG. 7. The program then proceeds to the next voxel in each ray (n=n+1), as at 86, and repeats the above steps by adding the corresponding 1-, 2-, or 3-bit number to the same registers. As noted above, the registers are hardwired to perform number addition, so the addition operation occurring at all of the registers can take place fill rates of 1 Gpixels/second. At each addition step, and for each ray in parallel, the program adds the next 8-bit voxel value to the associated four registers, and this process is continued until all voxels along all rays have been considered, as at 88.

To obtain the final density value for each pixel, the values of the four registers are summed, preserving the order of the original assignment of digits, as at 90 in FIG. 7. That is, any carry over from the register containing the lowest-value digits is added to the register containing the next-higher-value bits, which is added to the register with the next-higher-value bits and so forth. The final summed value, which will typically be a 24–32 bit number, may then be scaled to an 8-bit number, as at 92 in FIG. 7, and placed in the screen's gray-scale registers, to display the virtual image in gray scale, as at 94 in FIG. 7.

From the foregoing, various advantages and features of the invention can be appreciated. The mapping method, because it utilizes parallel addition in a slice-by-slice manner along the scanned tissue volume, and takes advantage of the hardwired addition feature of the display screen registers, is approximately two orders of magnitude faster than would be achieved by treating the four color registers in each pixel as a 32-bit register, and successively summing 8-bit numbers in this expanded register. This is due to inherent parallelism of the method (all rays are operated on simultaneously) and straightforward implementation on off-the-shelf hardware. More realistic light transport models (e.g., involving X-ray scattering) can also be incorporated in this model.

The speed of operation allows for virtual fluoroscopic image generation in real time, in accordance with the method described in Section III below. For example, accumulating 512 values along each ray on a $512^2$ viewport requires $512^3$ or 128 MegaAdditions, hence a graphics adapter with 1 Gpixel fill rate can compute 8 DRRs in a single second. It also facilitates other digitally reconstructed radiograph (DDR) applications, such as the one described in the background of Section I. In one embodiment, the invention includes an improved registration method, such as described in U.S. Pat. No. 4,791,934, where the DRR is generated by the fast-mapping method described herein. Another application of the fast-mapping method is the virtual fluoroscopic method now to be discussed.

III. Virtual Fluoroscopic Imaging

In still another aspect, the invention provides a virtual fluoroscopic method and system for "imaging" subsurface patient tissue, e.g., the spinal region, during a surgical or diagnostic procedure on the patient. The aim of the method, in part, is to allow a surgeon to view fluoroscopic-like or shadowgraph-like images of a patient target region on a frequent or repeated basis, without exposing the patient and others in the surgical station to x-radiation. For example, when doing spinal surgery, the surgeon may need to make frequent checks on the point of entry of a tool, or the placement of an implant, or the angle or depth of a cut, by referring to a fluoroscopic image of the region. The present method allows frequent virtual fluoroscopic images to be generated from a selected point in the surgical station.

In a preferred embodiment of the method, employing the fast-mapping algorithm described in Section II, the surgeon can generate real-time images as the virtual view position and orientation is adjusted. This allows the surgeon, for example, to move the virtual view point about the patient until an optimal fluoroscopic view of the surgical site is obtained, and then take an actual fluoroscopic image from the optimal position and orientation.

The system for carrying out the invention generally includes the components shown in FIG. 1 and in particular, a scan data file 18, computational device 20, and display device 24. As described above, the scan file consists of voxel coordinates, corresponding scan-data, e.g., density values, for each voxel, and coordinates for registration features, e.g., selected bone features or fiducials. The scan data file is operatively connected to the computational device, e.g., computer or processor, which carries out the data processing operations of the system to be described.

Optionally, the system may contain a tracking system, such as the OTS described in Section I, which may include either or both of two user-held instruments discussed below with reference to FIGS. 8 and 9.

As in the system described in Section II, the display device is preferably a conventional computer color monitor having a display screen composed of an XY array of pixels, e.g., a 1280×1024 pixel array. The monitor provides, for each pixel, a plurality of N-bit registers, typically four 8-bit registers corresponding to blue, red, green, and alpha (grayscale) pixel input values.

Figure 8:
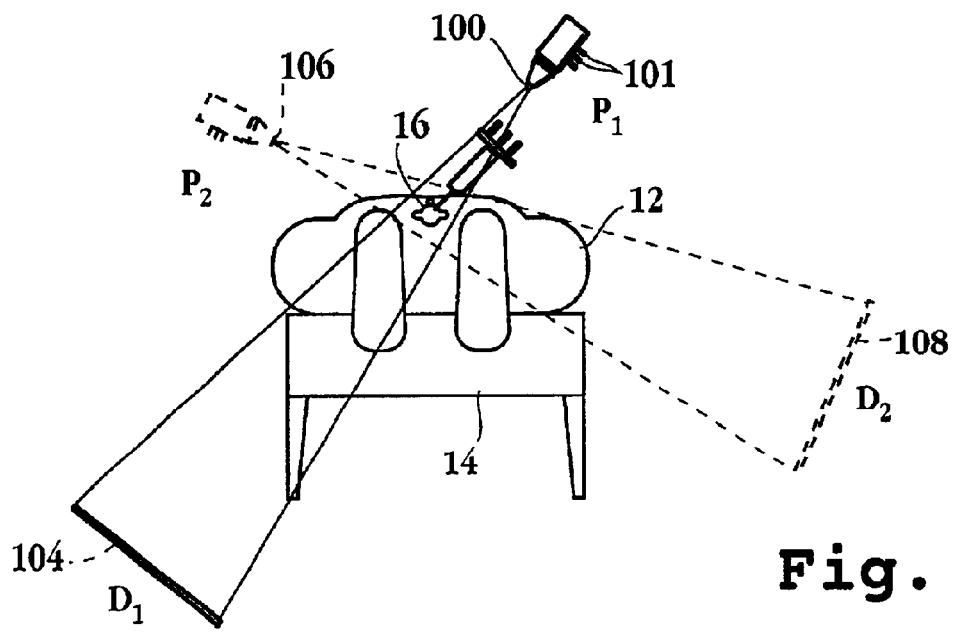
FIG. 8 illustrates the virtual fluoroscopy method of the invention, showing a virtual fluoroscopic source at two selected points.

FIG. 8 illustrates a surgical setting in which a patient 12 placed on a surgical bed 14 is undergoing spinal surgery at the target region indicated at 16. The figure shows a hand-held pointer 100 having tracking members, such as LEDs 101, for tracking the position and orientation of the pointer in space, through a suitable sensing device (not shown) such as the OTS described above. In the setting shown, it is assumed that the surgeon wishes to find an optimal view position and orientation for a fluoroscopic image, or simply wishes to view target structure by fluoroscopic-like images, e.g., for purposes of surgical planning.

Figure 10:
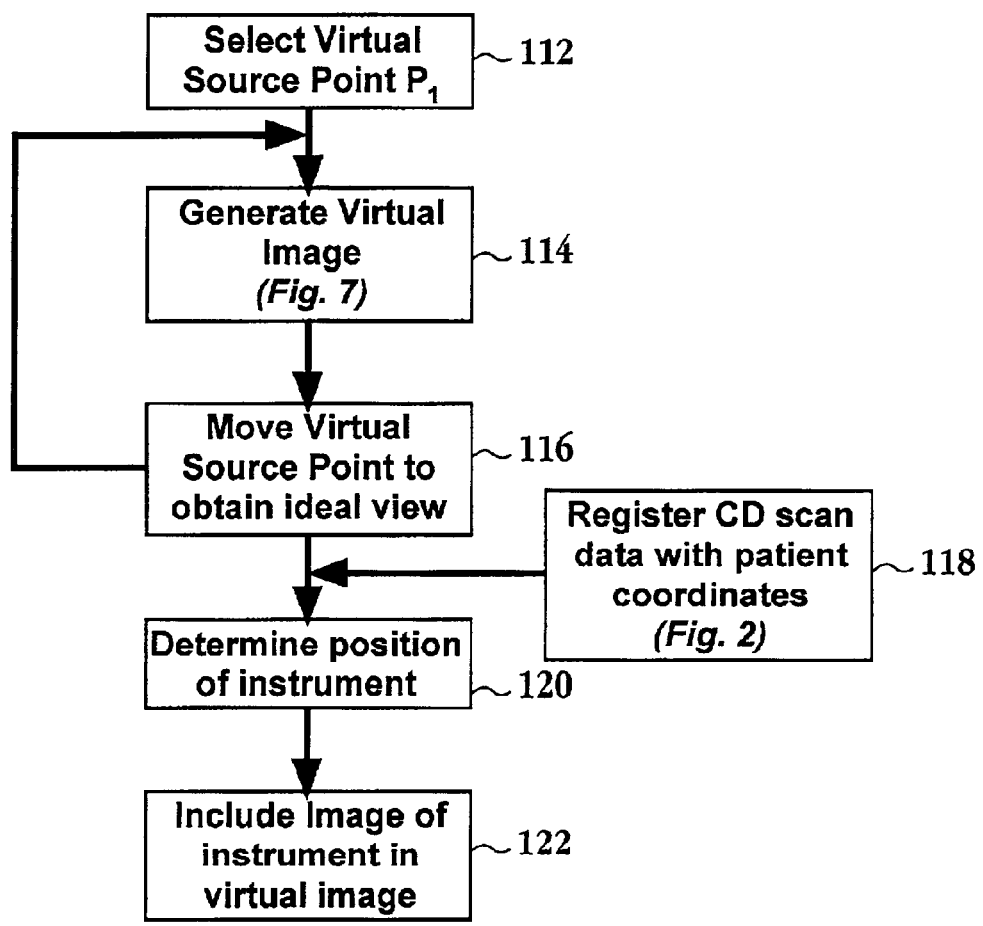
FIG. 10 is a flow diagram of the steps in the virtual fluoroscopy method of the invention.

In the method, the surgeon initially selects a desired point $P_1$, indicated at 102, and view orientation, as at 112 in FIG. 10. This is done, for example, by moving pointer 100 to a selected position and orientation, or by moving a frame-mounted pointer to a selected position and orientation. Upon user-activation, the system will then generate a virtual fluoroscopic image of the target tissue from the selected point and view orientation.

The system operates, as at 114 in FIG. 10, to generate the virtual image substantially by the method described in Section II, with reference to FIGS. 3 and 4, although not necessarily employing the fast-mapping algorithm described in Section II. Briefly, the system constructs a set of rays from the selected source point to the points in a virtual detector array, such as the virtual detector indicated at 104, and determines the sum of voxel density values along each ray from the scan data. The sum along each ray is then scaled, e.g., to an 8-bit number, and these values applied to the corresponding pixels in the display device, to generate a reconstructed shadowgraph image. As in Section II, the voxel coordinates may be precisely registered with the patient frame of reference, as at 118 in FIG. 10, in which case the reconstructed image precisely matches an actual fluoroscopic image from that position and orientation. If the scan data is not precisely registered with patient coordinates, the reconstructed image will be approximate only as to actual position.

In a preferred embodiment, the summing method applied to the voxel density values employs the fast mapping method described in Section II, where the summing operations are carried out by the individual registers up to the final summing of the values in the four different pixel registers. This method, because of its speed, allows reconstructed shadowgraph images in real time, as the user moves the pointer around in space. This allows the surgeon to quickly and efficiently find optimal views from which actual fluoroscopic images can be taken, or, if the scan data is in registry with patient coordinates, to view patient substructure accurately from continuously varying points of view, that is, with true x-ray vision.

Figure 9A:
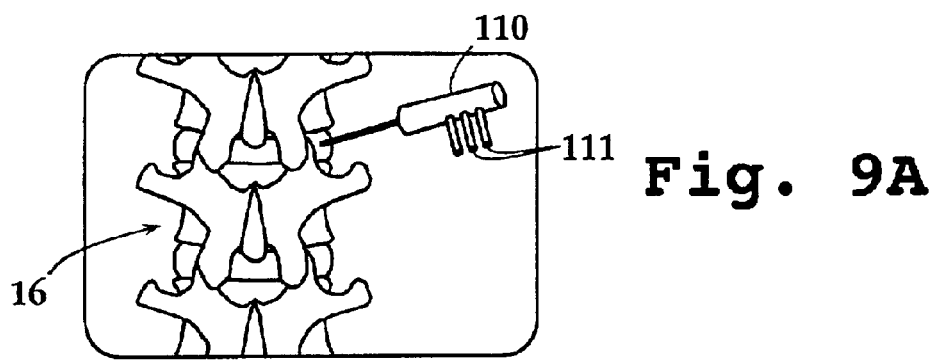
FIGS. 9A and 9B show views of a patient spinal column as generated by virtual fluoroscopy from the two virtual points shown in FIG. 8.
Figure 9B:
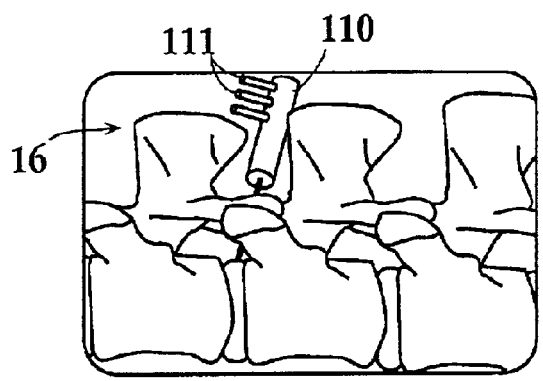

FIG. 8 shows selected views at points P1 (point 102) and P2 (point 106), and the virtual detector plates 104 and 108 associated with each view, as at 116 in FIG. 10. FIGS. 9A and 9B show corresponding reconstructed shadowgraph images of a patient spinal region seen from points $P_1$ and $P_2$, respectively, in accordance with the invention. Also shown in the figures is a surgical instrument 110 employed during a surgical position. Sensor elements, such as LEDs 111 on the instrument, are used for instrument tracking, as at 120 in FIG. 10, allowing the computer to reconstruct a virtual image of the instrument from its known position and superimpose this image on the reconstructed shadowgraph. In particular, with the scan data in registry with the patient coordinates, the user can view both hidden patient structure and the features of an instrument being employed in a surgical procedure, as at 122 in FIG. 10. Alternatively, or in addition, the surgical instrument can act as a pointer, to allow the surgeon to view target tissue from the position and orientation of the tool, to augment the information provided by the virtual fluoroscopic method.

Although the invention has been described with respect to particular components, operations, and applications, it will be appreciated that various modifications and changes may be made without departing from the invention as claimed. For example, a variety of tracking system may be employed from tracking the positions and orientations of various pointers, instruments and recorder plates in the surgical station, without affecting the overall result or operation of the claimed methods and systems.

What is claimed is:

1. A method for constructing from volumetric CT or MRI scan data of a patient region, a virtual two-dimensional fluoroscopic or shadowgraph image of the patient region as seen from a selected point in space, comprising (a) selecting a point in space representing a virtual fluoroscopic irradiation source, (b) defining a plurality of rays extending between the source point and each of a plurality of points in a two-dimensional XY array of points, where (i) the array points correspond to pixels in an XY pixel array in a display screen, (ii) each pixel in the display screen has multiple N-bit registers for receiving digitized values for each of multiple colors, (iii) the scan data is composed of voxels having defined coordinates and associated M-bit tissue-density values, and (iv) at least some of the rays pass through a plurality of such voxels in the patient target region, (c) for each ray, distributing the M bits of the density values of voxels along that ray among the multiple N-bit registers of the associated pixel, such that one or more bit positions of each M-bit value is assigned to a selected register of that pixel, (d) for each ray, summing the M-bit values of the voxels along that ray by (i) individually summing the one or more bit-position values in each associated pixel register, and (ii) determining the sum of the M-bit values along the associated ray from the values in the individual registers, and (e) displaying the image constructed of gray-scale values representing the summed M-bit density values at each pixel in said display screen.

2. The method of claim 1, wherein the pixels in the display screen each contain four 8-bit registers, the density values in each voxel are 8-bit numbers, and the 8 bit voxel-density numbers are distributed two digits each to each of the registers.

3. The method of claim 1, wherein the pixels in the display screen each contain four 8-bit registers, the density values in each voxel are 8-bit numbers, and the 8 bit voxel-density numbers are distributed 3 digits, 3 digits, 1 digit and 1 digit to each of the four registers.

4. A system for constructing from volumetric CT or MRI scan data of a patient region, a virtual two-dimensional fluoroscopic image of the patient region as seen from a selected point in space, comprising (a) a scan-data file for storing, in digital form, volumetric scan data of a surgical site of a patient, where the scan data is composed of voxels having defined coordinates and associated M-bit tissue-density values, (b) a display screen containing a two-dimensional XY array of pixel elements, each element containing multiple N-bit registers for receiving digital-scale values for each of multiple colors, and (c) a computational device operatively connected to the data file and display screen for (i) defining a plurality of rays extending between a selected source point and each of a plurality of points in a two-dimensional XY array, where (ia) the array points correspond to array pixels in the display screen, and (ib) at least some of the rays pass through a plurality of scan-date voxels in the patient target region, (ii) for each ray, distributing the M bits of the voxel density values among the multiple N-bit registers of the associated pixel, such that one or more bit positions of each M-bit value is assigned to a selected register of that pixel, (iii) for each ray, summing the M-bit values of the voxels along that ray by (iiia) individually summing the one or more bit-position values in each associated pixel register, and (iiib) determining the sum of the M-bit values along the associated ray from the values in the individual registers, and (iv) applying the summer tissue-density values along each ray to the associated pixel in the display screen.

5. A method of constructing a virtual two-dimensional image of a patient region as seen from a selected point in space from volumetric CT or MRI scan data of the patient region, the method comprising:

selecting a point in space representing a virtual fluoroscopic irradiation source;

defining a plurality of rays extending between the point in space and each of a plurality of points in a two-dimensional XY array of points;

distributing M-bits of tissue-density values of voxels along each ray among multiple N-bit registers of an associated pixel;

summing the M-bit values of the voxels along each ray; and displaying an image constructed of gray-scale values representing the summed M-bit density values at each pixel in a display screen.

6. The method of claim 5, wherein the array points correspond to pixels in an XY pixel array in the display screen, each pixel in the display screen having multiple N-bit registers for receiving digitized values for each of multiple colors, the scan data being composed of voxels having defined coordinates and associated M-bit tissue-density values, and at least some the rays passing through a plurality of the voxels in the patient target region.

7. The method of claim 5, wherein said distributing comprises assigning a selected register of a pixel to one or more bit positions of each M-bit value.

8. The method of claim 5, wherein said summing comprises individually summing one or more bit position values in an associated pixel register; and determining the sum of the M-bit values along the associated ray from the values in individual registers.

9. A system for constructing a virtual two-dimensional image of a patient region as seen from a selected point in space from volumetric CT or MRI scan data of the patient region, the system comprising:

a scan-data file for digitally storing volumetric scan data of a surgical site of a patient;

a display screen containing two-dimensional XY array of pixel elements; and a computational device operatively connected to the scan-data file and the display screen, said computational device defining a plurality of rays extending between a selected source point and each of a plurality of points in a two-dimensional XY array and said computational device distributing M bits of voxel density values among multiple N-bit registers of an associated pixel, such that one or more bit positions of each M-bit value is assigned to a selected register of that pixel.

10. The system of claim 9, wherein the scan data is composed of voxels having defined coordinates and associated M-bit tissue-density values.

11. The system of claim 9, wherein each element contains multiple N-bit registers for receiving digital-scale values for each of multiple colors.

12. The system of claim 9, wherein the plurality of points in the two-dimensional XY array correspond to array pixels in the display screen, and at least some of the rays pass through a plurality of scan-data voxels in patient region.

13. The system of claim 9, wherein said computational device sums the M-bit values of the voxels along that ray by individually summing the one or more bit-position values in each associated pixel register, and wherein the computational device determines the sum of the M-bit value along the associated ray from the values in the individual registers, and applies the tissue-density values along each ray to the associated pixel in the display screen.

14. A method of planning a surgical procedure, comprising:

forming a virtual two-dimensional images from at least one of volumetric CT and MRI data by:

(a) selecting point in space representing a virtual fluoroscopic irradiation source, (b) defining a plurality of rays extending between the point in space and each of a plurality of point in a two-dimensional XY array points, (c) distributing M-bits of tissue-density values of voxels along each ray among multiple N-bit registers of an associated pixel, and (d) summing the M-bit values of the voxels along each ray;

correlating the virtual two-dimensional images to at least one of CT and MRI images; and providing a virtual path of said surgical procedure through said correlating.

15. The method of claim 14, further comprising displaying an image constructed of gray-scale values representing the summed M-bit density values at each pixel in a display screen.

* * * * *